(12) United States Patent
Rekers et al.

(10) Patent No.: US 8,217,190 B2
(45) Date of Patent: Jul. 10, 2012

(54) PROCESSES FOR THE PRODUCTION OF ETHYLENE OXIDE AND ETHYLENE GLYCOL

(75) Inventors: Dominicus Maria Rekers, Amsterdam (NL); Abraham Adriaan Smaardijk, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1196 days.

(21) Appl. No.: 12/017,955

(22) Filed: Jan. 22, 2008

(65) Prior Publication Data
US 2008/0182999 A1    Jul. 31, 2008

(30) Foreign Application Priority Data

Jan. 22, 2007    (EP) ..................................... 07250250

(51) Int. Cl.
C07D 301/03    (2006.01)
C07C 43/00     (2006.01)
C07C 29/00     (2006.01)

(52) U.S. Cl. ......... 549/523; 549/538; 568/867; 568/613
(58) Field of Classification Search ................... 549/538, 549/523, 534; 568/867, 613, 621
See application file for complete search history.

(56) References Cited

U.S. PATENT DOCUMENTS

| | | | |
|---|---|---|---|
| 4,349,417 A | 9/1982 | Rebsdat et al. | 203/33 |
| 4,822,926 A | 4/1989 | Dye | 568/867 |
| 5,336,791 A | 8/1994 | Jennings et al. | 549/538 |
| 6,184,423 B1 | 2/2001 | Jen | 568/854 |
| 6,437,199 B1 | 8/2002 | Oka et al. | 568/867 |

OTHER PUBLICATIONS

"Ethylene Oxide" entry of Ullmann's Encyclopedia of Industrial Chemistry (1987 edition).

*Primary Examiner* — Taylor Victor Oh (57) ABSTRACT

The invention provides a process for the production of ethylene oxide and, optionally, ethylene glycol. A base is added at various positions downstream of the quench section of an ethylene oxide absorber. This mitigates corrosion in the ethylene oxide and ethylene glycol plant.

25 Claims, 3 Drawing Sheets

PROCESSES FOR THE PRODUCTION OF ETHYLENE OXIDE AND ETHYLENE GLYCOL

CROSS-REFERENCE TO RELATED APPLICATIONS

This application claims the benefit of European Patent Application No. 07250250.3, filed Jan. 22, 2007, which is incorporated herein by reference in its entirety.

FIELD OF THE INVENTION

The present invention relates to a process for the production of ethylene oxide and to a process for the production of ethylene glycol.

BACKGROUND OF THE INVENTION

Ethylene oxide (EO) is used as a chemical intermediate, primarily for the production of ethylene glycols (EG) but also for the production of ethoxylates, ethanol-amines, solvents and glycol ethers. It is produced by the direct oxidation of ethylene with oxygen or air. Ethylene and oxygen are passed over a silver catalyst, typically at pressures of 10-30 bar and temperatures of 200-300° C. The reaction is exothermic and a typical reactor consists of large bundles of several thousand tubes that are packed with catalyst. A coolant surrounds the reactor tubes, removing the reaction heat and permitting temperature control.

The product stream from the ethylene oxide reactor is supplied to an ethylene oxide absorber. The absorber has an initial quench section wherein the product stream is contacted with a cooled, recirculating aqueous quench stream and a basic solution is continuously added to the recirculating quench stream. Such a quench section is described in U.S. Pat. No. 4,822,926. The aqueous quench stream is said to neutralise acidic compounds such as acetic acid and formic acid that may have been formed in the reactor. Another quench section is described in U.S. Pat. No. 5,336,791.

The gas stream passes from the quench section to the main section of the ethylene oxide absorber where it is scrubbed with water to recover ethylene oxide. The resulting water stream, which is rich in ethylene oxide, is referred to as the fat absorbent and this is sent to an ethylene oxide stripper. In the ethylene oxide stripper, the ethylene oxide is stripped and a concentrated ethylene oxide stream is sent to ethylene oxide finishing processes such as condensation, distillation and re-absorption. The remaining liquids, referred to as the lean absorbent, are recycled to the ethylene oxide absorber.

High purity ethylene oxide can be chilled, stored and transported to customers. Alternatively, the ethylene oxide produced in the plant may be routed to an ethylene glycol unit. Ethylene glycol is typically manufactured by reacting ethylene oxide with an excess of water, typically at temperatures of 150-250° C. Under these conditions reaction rates are fast and no catalyst is required.

The reaction of ethylene oxide with water typically produces a glycol product stream consisting of almost 90 weight percent monoethylene glycol, the remainder being predominantly diethylene glycol, some triethylene glycol and a small amount of higher homologues. The glycol product stream is passed through successive distillation columns with decreasing pressure to remove water, which is returned to the ethylene glycol reactor. The mono-, di- and tri-ethylene glycol are separated by vacuum distillation.

Carbon steel has typically been used for reactor vessels and piping in ethylene oxide and ethylene glycol plants. In the "Ethylene Oxide" entry of Ullmann's Encyclopedia of Industrial Chemistry (1987 edition) it is stated that since ethylene oxide is noncorrosive, the reactors and the sections of the plant that convey ethylene oxide are usually made of mild steel. However, the present inventors have observed corrosion of sections of ethylene oxide/ethylene glycol (EO/EG) plants and have sought to understand the mechanism of this corrosion and thereby provide solutions for mitigating this corrosion.

SUMMARY OF THE INVENTION

Accordingly, the present invention provides a process for the production of ethylene oxide and, optionally, ethylene glycol comprising steps of (i) supplying ethylene and oxygen to an ethylene oxide reactor wherein ethylene and oxygen react to produce ethylene oxide, thereby producing a reactor product stream;

(ii) supplying the reactor product stream to an ethylene oxide absorber having a quench section and an absorber section downstream of the quench section, wherein the reactor product stream is contacted with a recirculating aqueous solution in the quench section and a base is added to the recirculating aqueous solution, and wherein ethylene oxide is recovered from the reactor product stream by absorption in water in the absorber section, thereby producing a fat absorbent stream;

(iii) supplying the fat absorbent stream to an ethylene oxide stripper wherein the fat absorbent stream is steam stripped, thereby producing a concentrated ethylene oxide stream and a lean absorbent stream;

(iv) recirculating the lean absorbent stream to the ethylene oxide absorber, and optionally, adding a base to the lean absorbent stream; and (v) optionally, supplying the concentrated ethylene oxide stream to an ethylene oxide finishing unit, thereby producing a purified ethylene oxide stream; and (vi) optionally, supplying the concentrated ethylene oxide stream, the purified ethylene oxide stream or any other ethylene oxide-containing stream to an ethylene glycol plant, producing ethylene glycol, wherein the ethylene glycol plant comprises an ethylene glycol reactor, a multistage evaporator system, a drying column, and a fractional distillation system, and wherein a water recycle stream passes from the multistage evaporator system to the ethylene glycol reactor and a water-depleted ethylene glycol stream passes from the multistage evaporator to the drying column, and optionally, a base is added to the water recycle stream;

wherein the process comprises the additional step of (vii) adding a base at one or more positions downstream of the quench section of the ethylene oxide absorber in at least one region where glycol esters are hydrolysed to organic acid and ethylene glycol other than the regions of the lean absorbent stream and the water recycle stream passing from the evaporator system to the ethylene glycol reactor. Preferably, the base is added such that the pH is maintained in the range of 5.5 to 9.5.

In an embodiment of the present invention, the ethylene oxide process includes withdrawing an aqueous quench bleed from the quench section; treating the aqueous quench bleed to remove or recover ethylene oxide, to recover ethylene glycol, and to remove heavies; and adding a base into the aqueous quench bleed either before or after it is treated to remove or recover ethylene oxide. Preferably, the base is added such that a pH is maintained in the range of 5.5 to 9.5.

In another embodiment of the present invention, the ethylene glycol process includes supplying the concentrated ethylene oxide stream, the purified ethylene oxide stream or any other ethylene oxide-containing stream to an ethylene glycol plant, producing glycol, wherein the ethylene glycol plant comprises an ethylene glycol reactor, a multistage evaporator system, a drying column, and a fractional distillation system, and wherein a water recycle stream passes from the multistage evaporator system to the ethylene glycol reactor and a water-depleted ethylene glycol stream passes from the multistage evaporator to the drying column; and adding a base into the water-depleted ethylene glycol stream and/or into the fractional distillation system. Preferably, the base is added such that the pH is maintained in the range of 5.5 to 9.5.

DETAILED DESCRIPTION OF THE INVENTION

The inventors have studied the corrosion of ethylene oxide/ethylene glycol plants and have identified a mechanism by which the corrosion occurs. They have also devised methods of mitigating the corrosion.

The inventors have surprisingly found that salts of organic acids that are present in the ethylene oxide absorber react with ethylene oxide to form glycol esters. For example for formate salts:

The sodium salt is present if the basic solution supplied is sodium hydroxide; if another base is used, another salt will be present. These glycol esters are transported downstream of the ethylene oxide absorber to many points in the ethylene oxide/ethylene glycol plant and, under certain conditions (typically conditions that are lean in ethylene oxide and rich in water) the glycol esters hydrolyse to form the organic acid plus ethylene glycol, e.g:

This production of acid creates an acidic environment at any point in the plant wherein the conditions promote hydrolysis. Although the concentration of salts of organic acids in the ethylene oxide absorber is low, continued hydrolysis of the glycol esters in positions downstream of the ethylene oxide absorber can lead to a gradual increase in organic acids and a resulting decrease in pH. The pH can reach levels (e.g. below pH 4) that lead to corrosion of the plant.

In many ethylene oxide plants, the lean absorbent is exposed to an open cooling tower, but for environmental reasons newer plants tend to have closed cooling systems. The inventors believe that in systems with an open cooling tower, most of the acids and glycol esters evaporate and therefore there is little acid formation by hydrolysis of the glycol ester downstream of the ethylene oxide absorber. In newer systems with a closed cooling system, the acids and glycol esters cannot evaporate and the levels of acid downstream of the ethylene oxide absorber can locally increase such that significant corrosion can occur. Additionally, in systems with open cooling systems it is necessary to add significant quantities of make-up water to the ethylene oxide absorber because water is lost to the atmosphere. This make-up water contains low levels of amines or other chemicals to control the make-up water pH. These amines or other chemicals can neutralise acids formed by hydrolysis of glycol esters, so the addition of make-up water may lessen the effect of ester hydrolysis and decrease corrosion. With closed cooling systems, much less make-up water is required so the concentration of amines or other chemicals will be lower and neutralisation of acids would be reduced accordingly with possible increase of corrosion.

One method of preventing acid corrosion is to replace carbon steel units with stainless steel units, but this is an expensive option and even stainless steel will corrode if exposed to low enough pH over extended periods. The present inventors have identified that acid corrosion occurs where glycol ester hydrolysis occurs and have been able to mitigate this corrosion by identifying various regions where glycol ester hydrolysis occurs and adding a base accordingly. This targeted approach is readily implemented once the regions of ester hydrolysis have been identified and enables continued use of carbon steel units even in systems with closed cooling systems. Until the identification of the glycol ester hydrolysis mechanism by the present inventors, the positions where base addition might have been contemplated downstream of the quench section of the ethylene oxide absorber are the large volume, mainly aqueous streams such as the lean absorbent recycle stream passing from the ethylene oxide stripper to the ethylene oxide absorber and the water recycle stream passing from the evaporator system to the ethylene glycol unit. The present inventors have surprisingly found that there can be significant changes in pH in various additional regions of ethylene oxide/ethylene glycol plants. They have identified a mechanism that explains the pH changes and have developed an effective means of preventing corrosion in ethylene oxide/ethylene glycol plants.

The reaction of ethylene and oxygen to produce ethylene oxide in an ethylene oxide reactor is well known to the skilled person. The oxygen may be supplied as oxygen or as air, but is preferably supplied as oxygen. Ballast gas, for example methane, is typically supplied to allow operation at high oxygen levels without causing a flammable mixture. Inhibitor, e.g. monochloroethane or dichloroethane, may be supplied for catalyst performance control. The ethylene, oxygen, ballast gas and inhibitor are preferably supplied to recycle gas that is supplied to the ethylene oxide reactor from the ethylene oxide absorber.

The ethylene oxide reactor is suitably a multitubular, fixed bed reactor. The catalyst is preferably finely dispersed silver and optionally promoter metals on a support material, for example, alumina. The reaction is preferably carried out at pressures of greater than 10 bar and less than 30 bar and temperatures of greater than 200° C. and less than 300° C.

Most of the ethylene reacts to form ethylene oxide, but a portion of the ethylene will be oxidised fully, providing carbon dioxide and water. The reactor product stream is supplied to the quench section of an ethylene oxide absorber. In the quench section, the reactor product stream is contacted with a recirculating aqueous solution and a base is added to the recirculating aqueous solution. The base is preferably an aqueous alkaline solution, for example sodium hydroxide or potassium hydroxide solution, most preferably sodium hydroxide solution. The concentration of the alkaline solution is preferably from 5 to 50 wt %, most preferably from 10 to 30 wt %. Subsequently, the gases pass to the absorber section wherein ethylene oxide is recovered from the reactor product stream by absorption in water. An example of an ethylene absorber having a quench section is described in U.S. Pat. No. 4,822,926.

In a preferred embodiment, an aqueous quench bleed is withdrawn from the quench section, preferably from the recirculating aqueous solution. The quench bleed typically contains a low concentration of ethylene oxide, a low concentration of ethylene glycol and salts such as sodium carbonate and bicarbonate. The quench bleed is typically treated to remove or recover ethylene oxide, to recover ethylene glycol and to remove heavies such as sodium salts. For example, the quench bleed may be treated as described in U.S. Pat. No. 4,822,926: the quench bleed is passed to a pipe reactor wherein ethylene oxide is hydrolysed to ethylene glycol, the resulting dilute aqueous ethylene glycol solution is passed to a flasher wherein water is evaporated, the resulting two-phase slurry containing stream is passed to a centrifuge and the resulting centrifuged liquid phase is passed to a glycol bleed flasher.

Preferably, overhead vapours from the ethylene oxide absorber are recycled to the ethylene oxide reactor. A portion of this recycle gas is preferably diverted through a scrubber for carbon dioxide removal and is then returned to the recycle stream. A vent stream is typically taken from the recycle gas to reduce the build-up of inerts such as ethane, argon and nitrogen and to remove impurities.

The aqueous stream exiting the ethylene oxide absorber, the fat absorbent stream, is supplied to an ethylene oxide stripper. In a typical ethylene oxide stripper, a concentrated ethylene oxide stream leaves the top of the stripper and a lean absorbent stream leaves the bottom of the stripper. The lean absorbent stream is recirculated to the ethylene oxide absorber. Preferably, a base, as described herein, is added to the lean absorbent stream before being supplied to the ethylene oxide absorber. Preferably, the lean absorbent stream is cooled before it is supplied to the ethylene oxide absorber.

In a preferred embodiment of the invention, the cooling of the lean absorbent stream occurs in a closed cooling system. Many prior art systems use open cooling systems but it is preferred, for environmental reasons, to use closed cooling systems. With a closed cooling system, corrosion can occur as the acids and glycol esters are not removed by evaporation, and glycol esters can hydrolyse to form acids. However, in the process of the present invention corrosion is prevented by dosing with base to maintain pH in the range of 5.5 to 9.5 in regions where the esters are hydrolysed.

The process preferably further comprises a step of taking a slip stream of the lean absorbent and supplying the slip stream to a glycol recovery unit wherein glycols are recovered. Glycol production is typically low, but without removal of a slip stream, glycol content in the recirculating lean absorbent would increase.

The concentrated ethylene oxide stream that leaves the top of the ethylene oxide stripper is optionally supplied to an ethylene oxide finishing unit, providing a purified ethylene oxide stream. The finishing unit preferably consists of condensation, distillation and re-absorption units.

The purified ethylene oxide stream may be chilled and routed to storage (ethylene oxide is generally stored under a nitrogen blanket at approximately 10° C.).

The process of the invention provides a number of ethylene oxide containing streams, and any of these streams can be supplied to an ethylene glycol plant. In typical EO/EG plants a number of different streams, including the concentrated ethylene oxide stream, will be supplied to the ethylene glycol plant. It is possible, but not preferred, to supply the purified ethylene oxide stream to the ethylene glycol plant. The ethylene glycol plant typically consists of an ethylene glycol reactor, a multistage evaporator system, a drying column and a fractional distillation system.

The ethylene glycol reactor is preferably a noncatalytic reactor wherein ethylene oxide and water react at a temperature from 150 to 250° C. and a pressure from 30 to 40 atmospheres. The ethylene glycol reactor may alternatively be a catalytic reactor. In a noncatalytic reactor, it is preferred to use an excess of water, for example a molar ratio of 1:22 ethylene oxide to water.

The ethylene glycol product stream emerging from the ethylene glycol reactor is preferably supplied to a multistage evaporator system wherein excess water is removed. Water that is removed in the multistage evaporator system is preferably supplied to the ethylene glycol reactor. Preferably, a base, as described herein, is added to this water recycle stream to the ethylene glycol reactor.

Further water is preferably removed in a drying column. The water depleted ethylene glycol stream typically consists of 70 to 95 weight % monoethylene glycol, with the remainder being diethylene glycol and triethylene glycol and is supplied to a fractional distillation system wherein the individual glycol products are recovered at high purity level.

The base that is added in the process of the invention is preferably an aqueous alkaline solution, for example sodium hydroxide or potassium hydroxide solution. Potassium hydroxide may be preferred because potassium salts are more soluble than sodium salts and therefore cause less fouling in units such as the re-boilers in an ethylene glycol plant. However, sodium hydroxide is less expensive than potassium hydroxide so it may be preferred, particularly if there is no diethylene glycol and or triethylene glycol recovery. The concentration of the aqueous alkaline solution is preferably from 5 to 50 wt %, more preferably from 10 to 30 wt %. The aqueous alkaline solution is a liquid and is added to liquids (i.e. it is not added to reactants or products in the gaseous phase). It may be preferable to use an organic base, typically an amine, for addition at points in the ethylene glycol plant, particularly into water that is recycled from the evaporator system to the ethylene glycol reactor. However, amines are not preferred in the ethylene oxide plant as they could affect the activity of the catalyst.

The base is added to maintain the pH in the range of from 5.5 to 9.5, preferably from 6 to 9 and most preferably from 6.5 to 8.5 in the various regions where glycol esters are hydrolysed to organic acid and ethylene glycol. Adding sufficient base to maintain the pH above 5.5 ensures that even though ester hydrolysis may be occurring, acid corrosion of the plant cannot occur. However, addition of too much base could increase the pH above 9.5 and this is also undesirable. In the ethylene oxide section of the plant, a pH above 9.5 can lead to carbonate stress corrosion of the plant. In ethylene glycol sections of the plant, a pH above 9.5 can reduce the quality of the ethylene glycol product. The pH at the various regions in the plant can be monitored using known techniques and pH measurement devices, including in-line pH measurement and sampling techniques.

In a preferred embodiment, the pH is maintained in the range of 5.5 to 9.5, preferably from 6 to 9 and most preferably from 6.5 to 8.5 in all regions where glycol esters are hydrolysed to organic acid and ethylene glycol. If there are any regions where glycol esters are hydrolysed to organic acid and ethylene glycol and the pH is not controlled, it is likely that the acidity will continue to increase in that region and corrosion will occur.

Regions where glycol esters are hydrolysed to organic acid and ethylene glycol can be identified using either chromatographic or spectroscopic techniques or pH analysis. With chromatographic or spectroscopic techniques, samples are taken from a variety of positions in the plant. The samples are analysed using techniques such as ion chromatography or infra-red spectroscopy. This enables the skilled person to quantify the amount of glycol esters and organic esters in the sample. By comparing results from samples from different positions it is possible to see where there is an increase in the organic acid content and a decrease in the glycol ester content and thereby identify where hydrolysis is occurring. With pH analysis, pH is measured at various positions in the plant and regions where hydrolysis is occurring are identified by finding regions where the pH is decreasing.

The regions where glycol ester hydrolysis occurs may vary from plant to plant, depending on the set-up of the plant and the conditions. Based upon a study of several plants, the present inventors have identified a number of regions where glycol ester hydrolysis is likely to occur: in the ethylene oxide stripper; in the flasher and subsequent sections in the quench bleed unit; in the glycol recovery unit (wherein a slip stream of the lean absorbent is supplied to the unit); and in the ethylene glycol reactor, multistage evaporator system, drying column and fractional distillation system of the ethylene glycol plant.

The positions and the amounts of base that are added are determined by the requirement to control pH in the various regions where glycol ester hydrolysis occurs. Base is preferably added at multiple positions to enable control of pH at multiple regions where glycol ester hydrolysis occurs, more preferably base is added at one or more positions where glycol ester hydrolysis occurs in addition to any base that may be added to the lean absorbent stream and the water recycle stream passing from the evaporator system to the ethylene glycol reactor. Base is preferably added in the ethylene oxide stripper or at three or more positions downstream of the ethylene oxide stripper wherein two of the positions are the lean absorbent stream and the water recycle stream passing from the evaporator system to the ethylene glycol reactor.

The present inventors suggest that pH can be controlled between 5.5 and 9.5 in the regions where ester hydrolysis occurs by addition of base at one or more of the following positions:

(a) if a quench bleed is withdrawn from the quench section, into the quench bleed draw off from the ethylene oxide absorber, or downstream of the point where ethylene oxide is removed (b) into the fat absorbent stream (c) into the ethylene oxide stripper (d) if a slip stream of the lean absorbent is supplied to a glycol recovery unit, into the slip stream to that recovery unit or into the recovery unit itself (e) if an EO finishing unit is used, in water rich and EO lean streams leaving an EO finishing unit (f) into the water depleted ethylene glycol stream resulting from the multistage evaporator (g) into the fractional distillation unit.

Preferably, the pH is controlled in positions a, b, c, e, and/or g.

Figure 1:
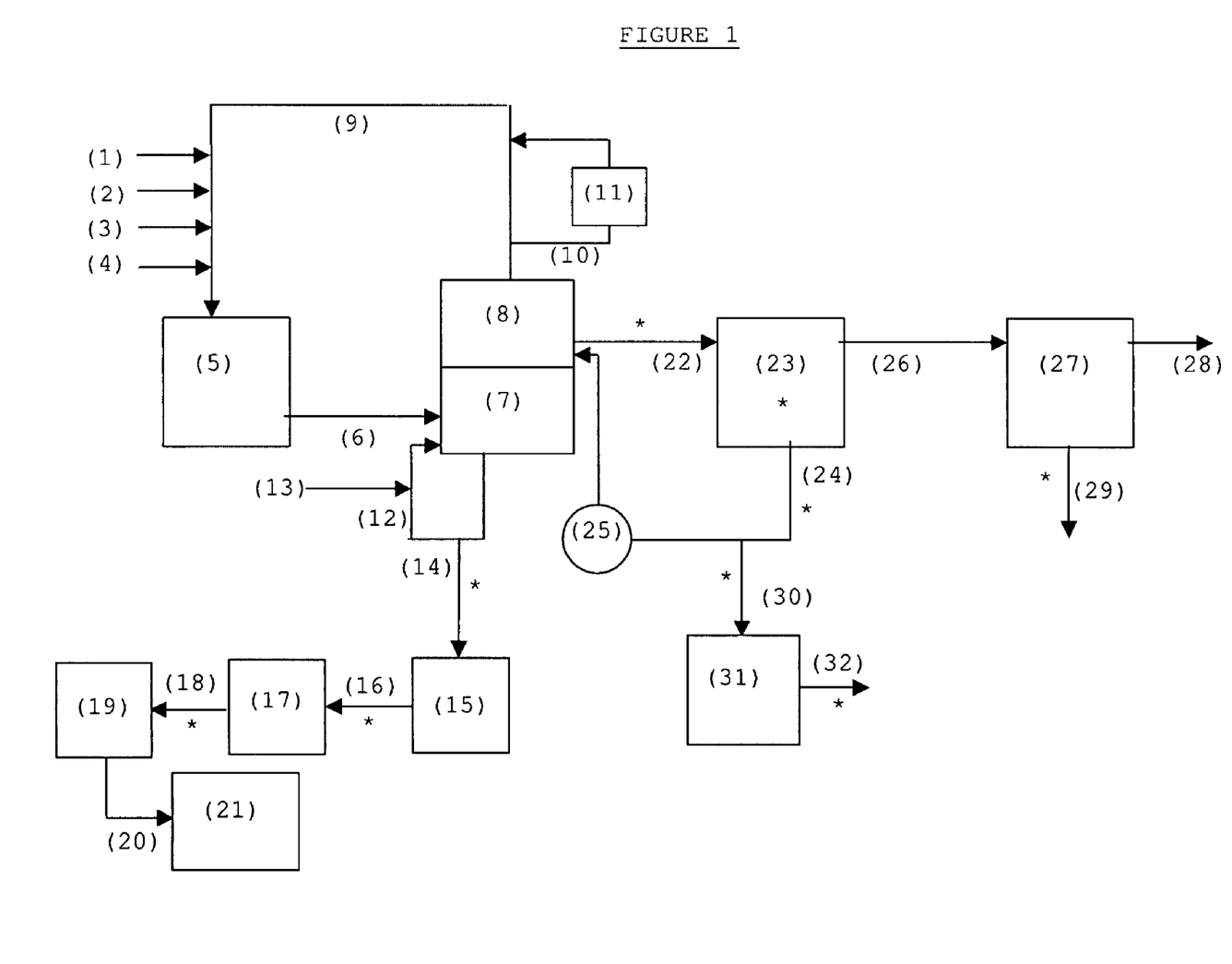
FIG. 1 is a schematic diagram showing a preferred embodiment of the process according to the invention for producing ethylene oxide.

FIG. 1 shows a preferred embodiment of the process of the invention for producing ethylene oxide. Ethylene (1), oxygen (2), methane (3) and monochloroethane (4) are supplied to a recycle gas stream (9) which is supplied to an ethylene oxide reactor (5). The ethylene oxide reactor (5) is a multitubular fixed bed reactor wherein the tubes are filled with silver catalyst on an alumina support. The reactor product stream (6) leaving the reactor (5) contains ethylene oxide, carbon dioxide, water and small amounts of impurities. The reactor product stream (6) is supplied to the quench section (7) and then the absorber section (8) of the ethylene oxide absorber (7,8). The overhead gases in the absorber section (8) are recycled (9) to the ethylene oxide reactor (5). A portion of the recycle gas stream (9) is diverted (10) via a scrubber (11) that removes carbon dioxide from the recycle gas. In the quench section (7), the reactor product stream (6) is contacted with a recirculating aqueous solution (12). Sodium hydroxide (13) is added to the recirculating aqueous solution (12).

A quench bleed (14) is withdrawn from the recirculating aqueous solution (12) and is passed to an ethylene oxide removal unit (15), which could be a pipe reactor wherein ethylene oxide is hydrolysed to ethylene glycol, producing a dilute aqueous ethylene glycol solution or could be an ethylene oxide stripper wherein ethylene oxide is stripped and sent back to the ethylene oxide absorber (7,8). A dilute solution containing ethylene glycol (16) is passed to a flasher (17) wherein water and ethylene glycol are evaporated and recovered. The remaining two-phase slurry containing stream (18) is passed to a centrifuge (19) and the resulting centrifuged liquid phase (20) is passed to a glycol bleed flasher (21). As an alternative to the centrifuge (19) and flasher (21), the stream (18) can be transported away from the plant and treated in an independent process.

The fat absorbent stream (22) that results from the ethylene oxide absorber (7,8) is supplied to the ethylene oxide stripper (23). Lean absorbent (24) from the ethylene oxide stripper (23) is recirculated to the ethylene oxide absorber (7,8) via a cooling system (25). The concentrated ethylene oxide stream (26) from the ethylene oxide stripper (23) is supplied to the ethylene oxide finishing unit (27), producing the purified ethylene oxide stream (28). The remaining water streams (29) can be sent back to the lean absorbent stream (24), can be sent to a glycol unit and/or can be sent to waste water.

A slip stream (30) of the lean absorbent (24) is supplied to a glycol unit (31), producing a glycol stream (32).

A base may be supplied at any location marked with a star (*). This includes into the fat absorbent stream (22), to the ethylene oxide stripper (23), to the lean absorbent stream (24), to the slip stream (30), to the water streams (29), to the quench bleed stream (14), to the dilute aqueous ethylene glycol solution (16), to the two-phase slurry containing stream (18) and to the glycol stream (32).

Figure 2:
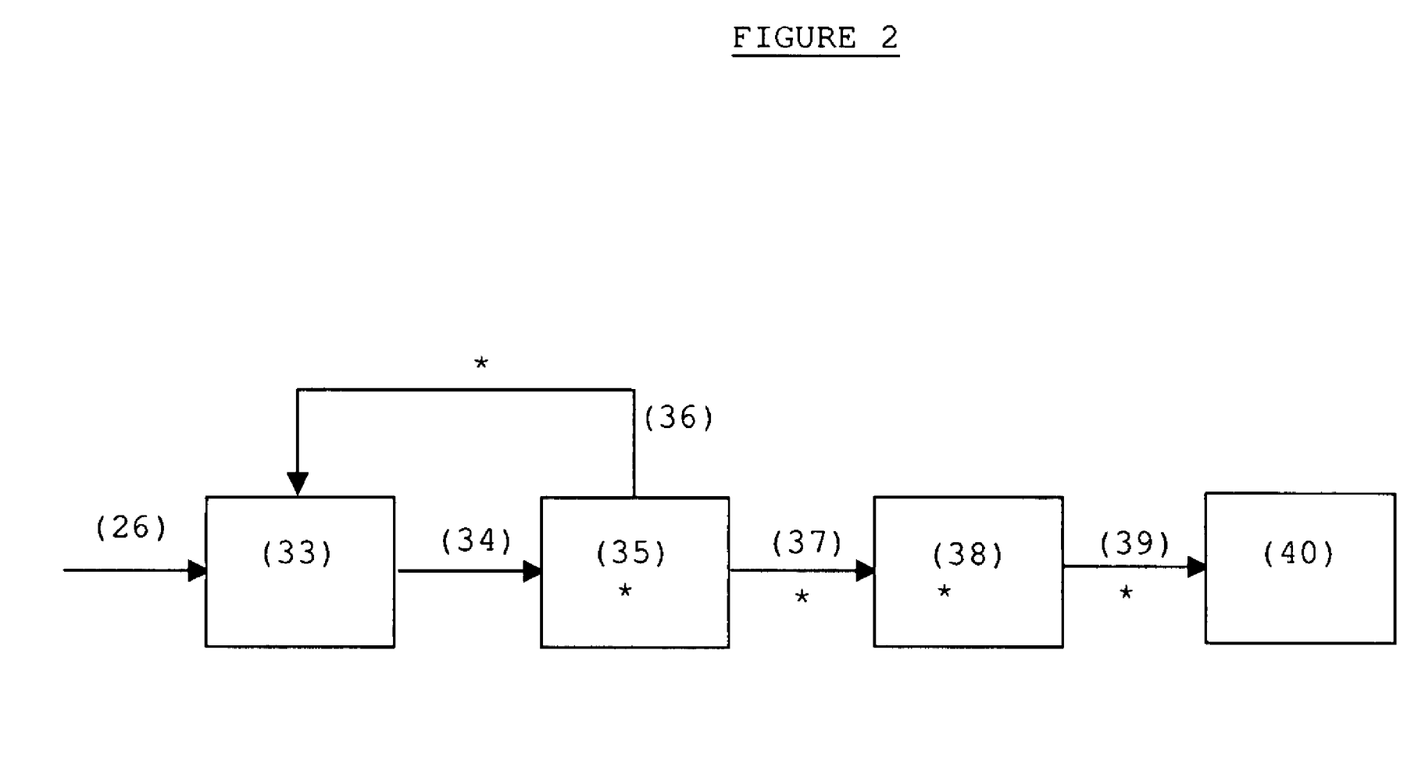
FIG. 2 is a schematic diagram showing a preferred embodiment of the process according to the invention for producing ethylene glycol, which can be combined with the process shown in FIG. 1 for producing ethylene oxide.

FIG. 2 shows a process for producing ethylene glycol, which can be combined with the process shown in FIG. 1 for producing ethylene oxide. Any ethylene oxide containing streams from the ethylene oxide plant of FIG. 1 (e.g. the concentrated ethylene oxide stream, (26), the lean absorbent stream (24), the water streams (29)) can be supplied to the ethylene glycol reactor (33), which is a noncatalytic pipe-type reactor. The ethylene glycol product stream (34) emerging from the ethylene glycol reactor is supplied to a multistage evaporator system (35). Water is removed in the multistage evaporator system (35) and is supplied to the ethylene glycol reactor (33). The ethylene glycol stream (37) is supplied to a drying column (38) wherein further water is removed. The water depleted ethylene glycol stream (39) is supplied to a fractional distillation system (40) wherein the individual glycol products are recovered at high purity level.

A base may be supplied at any location marked with a star (*). This includes into the evaporator system (35), into the water recycle (36) at any point including into water collection vessels in the recycle system, into the condensed ethylene glycol stream (37), into the drying column (38), into water depleted ethylene glycol stream (39).

Figure 3:
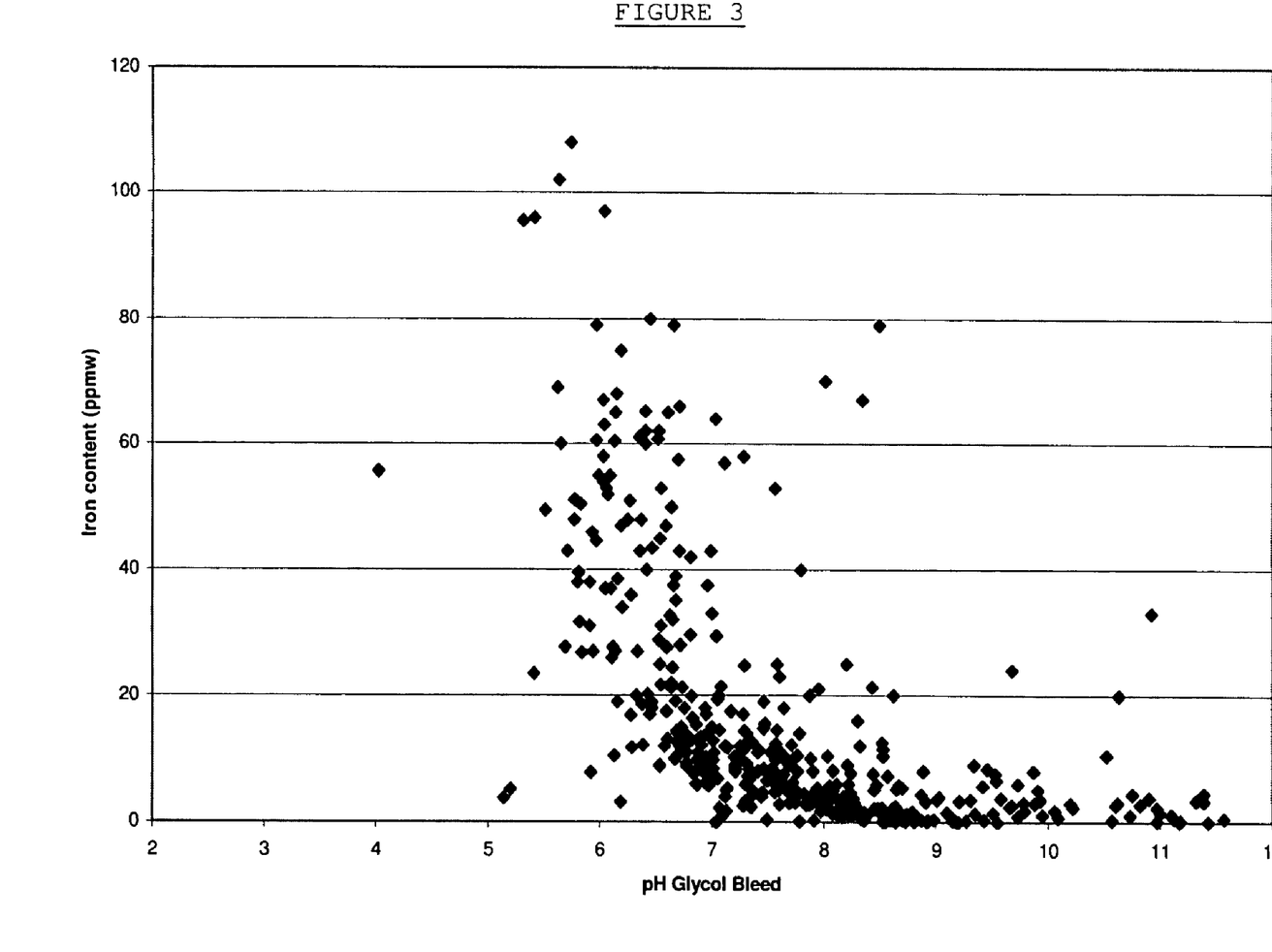
FIG. 3 is a graph showing the relationship between iron content and pH in a stream in an ethylene oxide plant.

FIG. 3 shows how the iron content of the glycol bleed stream (32 in FIG. 1) varies with the pH of the stream. Iron content increases as pH decreases and is particularly high when pH is below 6.5. This indicates that corrosion is very likely to occur if the pH of the bleed stream is below 6.5.

The inventors observed that high acidity in the quench bleed stream (14 in FIG. 1) meant that glycol produced in the downstream recovery units was off specification, having a high content of esters. Dosing an additional amount of sodium hydroxide solution into the quench bleed stream (14) solved that problem.

What is claimed is:

1. A process for the production of ethylene oxide and ethylene glycol comprising steps of
   (i) supplying ethylene and oxygen to an ethylene oxide reactor wherein ethylene and oxygen react to produce ethylene oxide, thereby producing a reactor product stream;
   (ii) supplying the reactor product stream to an ethylene oxide absorber having a quench section and an absorber section downstream of the quench section, wherein the reactor product stream is contacted with a recirculating aqueous solution in the quench section and a base is added to the recirculating aqueous solution, and wherein ethylene oxide is recovered from the reactor product stream by absorption in water in the absorber section, thereby producing a fat absorbent stream;
   (iii) supplying the fat absorbent stream to an ethylene oxide stripper wherein the fat absorbent stream is steam stripped, thereby producing a concentrated ethylene oxide stream and a lean absorbent stream;
   (iv) recirculating the lean absorbent stream to the ethylene oxide absorber;
   (v) supplying the concentrated ethylene oxide stream to an ethylene oxide finishing unit, thereby producing a purified ethylene oxide stream; and
   (vi) supplying the concentrated ethylene oxide stream, the purified ethylene oxide stream or any other ethylene oxide-containing stream to an ethylene glycol plant, producing ethylene glycol, wherein the ethylene glycol plant comprises an ethylene glycol reactor, a multistage evaporator system, a drying column, and a fractional distillation system, and wherein a water recycle stream passes from the multistage evaporator system to the ethylene glycol reactor and a water-depleted ethylene glycol stream passes from the multistage evaporator to the drying column;
   wherein the process comprises the additional step of
   (vii) adding a base at one or more positions downstream of the quench section of the ethylene oxide absorber in at least one region where glycol esters are hydrolyzed to organic acid and ethylene glycol other than the regions of the lean absorbent stream and the water recycle stream passing from the evaporator system to the ethylene glycol reactor.

2. The process as claimed in claim 1, wherein in step (vii), base is added such that the pH is maintained in the range of 5.5 to 9.5.

3. The process as claimed in claim 1, wherein in step (vii), the base is added into the fat absorbent stream and/or into the ethylene oxide stripper.

4. The process as claimed in claim 1, wherein the process further comprises withdrawing an aqueous quench bleed from the quench section and treating the aqueous quench bleed to remove or recover ethylene oxide, to recover ethylene glycol and to remove heavies.

5. The process as claimed in claim 4, wherein in step (vii), the base is added into the aqueous quench bleed either before or after it is treated to remove or recover ethylene oxide.

6. The process as claimed in claim 1, wherein the process further comprises taking a slip stream of the lean absorbent and supplying the slip stream of the lean absorbent to a glycol recovery unit wherein glycols are recovered, and wherein in step (vii), the base is added into the slip stream and/or into the glycol recovery unit.

7. The process as claimed in claim 1, wherein in step (vii), the base is added into the water-depleted ethylene glycol stream passing from the multistage evaporator to the drying column and/or into the fractional distillation system.

8. The process as claimed in claim 1, wherein in step (vii), the base is added into the evaporator system and/or into the drying column.

9. The process as claimed in claim 1, wherein the base is a sodium hydroxide and/or potassium hydroxide solution.

10. The process as claimed in claim 1, wherein the process further comprises the step of cooling the lean absorbent stream in a closed cooling system.

11. A process for the production of ethylene oxide and ethylene glycol comprising steps of
   (i) supplying ethylene and oxygen to an ethylene oxide reactor wherein ethylene and oxygen react to produce ethylene oxide, thereby producing a reactor product stream;
   (ii) supplying the reactor product stream to an ethylene oxide absorber having a quench section and an absorber section downstream of the quench section, wherein the reactor product stream is contacted with a recirculating aqueous solution in the quench section and a base is added to the recirculating aqueous solution, and wherein ethylene oxide is recovered from the reactor product stream by absorption in water in the absorber section, thereby producing a fat absorbent stream;
   (iii) withdrawing an aqueous quench bleed from the quench section and treating the aqueous quench bleed to remove or recover ethylene oxide, to recover ethylene glycol and to remove heavies;
   (iv) supplying the fat absorbent stream to an ethylene oxide stripper wherein the fat absorbent stream is steam stripped, thereby producing a concentrated ethylene oxide stream and a lean absorbent stream;
   (v) recirculating the lean absorbent stream to the ethylene oxide absorber; and
   (vi) supplying the concentrated ethylene oxide stream to an ethylene oxide finishing unit, thereby producing a purified ethylene oxide stream; and (vii) supplying the concentrated ethylene oxide stream, the purified ethylene oxide stream or any other ethylene oxide-containing stream to an ethylene glycol plant, producing ethylene glycol;

wherein the process comprises the additional step of (viii) adding a base into the aqueous quench bleed either before or after it is treated to remove or recover ethylene oxide.

12. The process as claimed in claim 11, wherein the base is added such that a pH is maintained in the range of 5.5 to 9.5.

13. The process as claimed in claim 11, wherein the process further comprises adding a base into the fat absorbent stream and/or into the ethylene oxide stripper.

14. The process as claimed claim 11, wherein the base is added after the aqueous quench bleed is treated to remove or recover ethylene oxide.

15. The process as claimed in claim 14, wherein the base is added into a dilute aqueous ethylene glycol solution exiting a ethylene oxide removal unit and/or into a two-phase slurry containing stream exiting a flasher unit.

16. The process as claimed in claim 11, wherein the process further comprises the step of cooling the lean absorbent stream in a closed cooling system.

17. The process as claimed in claim 11, wherein the base is a sodium hydroxide and/or potassium hydroxide solution.

18. A process for the production of ethylene oxide and ethylene glycol comprising steps of
  (i) supplying ethylene and oxygen to an ethylene oxide reactor wherein ethylene and oxygen react to produce ethylene oxide, thereby producing a reactor product stream;
  (ii) supplying the reactor product stream to an ethylene oxide absorber having a quench section and an absorber section downstream of the quench section, wherein the reactor product stream is contacted with a recirculating aqueous solution in the quench section and a base is added to the recirculating aqueous solution, and wherein ethylene oxide is recovered from the reactor product stream by absorption in water in the absorber section, thereby producing a fat absorbent stream;
  (iii) supplying the fat absorbent stream to an ethylene oxide stripper wherein the fat absorbent stream is steam stripped, thereby producing a concentrated ethylene oxide stream and a lean absorbent stream;
  (iv) recirculating the lean absorbent stream to the ethylene oxide absorber, and adding a base into the lean absorbent stream;
  (v) supplying the concentrated ethylene oxide stream to an ethylene oxide finishing unit, thereby producing a purified ethylene oxide stream; and
  (vi) supplying the concentrated ethylene oxide stream, the purified ethylene oxide stream or any other ethylene oxide-containing stream to an ethylene glycol plant, producing ethylene glycol, wherein the ethylene glycol plant comprises an ethylene glycol reactor, a multistage evaporator system, a drying column, and a fractional distillation system, and wherein a water recycle stream passes from the multistage evaporator system to the ethylene glycol reactor and a water-depleted ethylene glycol stream passes from the multistage evaporator to the drying column and a base is added into the water recycle stream;

wherein the process comprises the additional step of (vii) adding a base into the water-depleted ethylene glycol stream and/or into the fractional distillation system.

19. The process as claimed in claim 18, wherein the base is added such that the pH is maintained in the range of 5.5 to 9.5.

20. The process as claimed in claim 18, wherein the process further comprises adding a base into the evaporator system, and/or into the drying column.

21. The process as claimed in claim 18, wherein the process further comprises adding a base into the fat absorbent stream and/or into the ethylene oxide stripper.

22. The process as claimed in claim 18, wherein the process further comprises withdrawing an aqueous quench bleed from the quench section and treating the aqueous quench bleed to remove or recover ethylene oxide, to recover ethylene glycol and to remove heavies; and adding a base into the aqueous quench bleed either before or after it is treated to remove or recover ethylene oxide.

23. The process as claimed in claim 18, wherein the process further comprises the step of cooling the lean absorbent stream in a closed cooling system.

24. The process as claimed in claim 18, wherein the base is a sodium hydroxide and/or potassium hydroxide solution.

25. A process for the production of ethylene oxide and ethylene glycol comprising steps of
  (i) supplying ethylene and oxygen to an ethylene oxide reactor wherein ethylene and oxygen react to produce ethylene oxide, thereby producing a reactor product stream;
  (ii) supplying the reactor product stream to an ethylene oxide absorber having a quench section and an absorber section downstream of the quench section, wherein the reactor product stream is contacted with a recirculating aqueous solution in the quench section and a sodium hydroxide and/or potassium hydroxide solution is added to the recirculating aqueous solution, and wherein ethylene oxide is recovered from the reactor product stream by absorption in water in the absorber section, thereby producing a fat absorbent stream;
  (iii) withdrawing an aqueous quench bleed from the quench section and treating the aqueous quench bleed to remove or recover ethylene oxide, to recover ethylene glycol and to remove heavies;
  (iv) supplying the fat absorbent stream to an ethylene oxide stripper wherein the fat absorbent stream is steam stripped, thereby producing a concentrated ethylene oxide stream and a lean absorbent stream;
  (v) recirculating the lean absorbent stream to the ethylene oxide absorber and adding a sodium hydroxide and/or potassium hydroxide solution into the lean absorbent stream;
  (vi) taking a slip stream of the lean absorbent and supplying the slip stream of the lean absorbent to a glycol recovery unit wherein glycols are recovered; and
  (vii) supplying the concentrated ethylene oxide stream to an ethylene oxide finishing unit, thereby producing a purified ethylene oxide stream;
  (viii) supplying the concentrated ethylene oxide stream, the purified ethylene oxide stream or any other ethylene oxide-containing stream to an ethylene glycol plant, producing ethylene glycol, wherein the ethylene glycol plant comprises an ethylene glycol reactor, a multistage evaporator system, a drying column, and a fractional distillation system, and wherein a water recycle stream passes from the multistage evaporator system to the ethylene glycol reactor and a water-depleted ethylene glycol stream passes from the multistage evaporator to the drying column, and a sodium hydroxide and/or potassium hydroxide solution is added into the water recycle stream;

wherein the process comprises the additional step of
(ix) adding a sodium hydroxide and/or potassium hydroxide solution in at least one position selected from the group consisting of;
   (a) the aqueous quench bleed either before or after it is treated to remove or recover ethylene oxide,
   (b) the fat absorbent,
   (c) the ethylene oxide stripper,
   (d) the slip stream or glycol recovery unit,
   (e) the water rich and ethylene oxide lean streams leaving the ethylene oxide finishing unit,
   (f) the water-depleted ethylene glycol stream passing from the multistage evaporator to the drying column, and
   (g) the fractional distillation system.

* * * * *